United States Patent
Ho

(10) Patent No.: US 9,192,238 B2
(45) Date of Patent: Nov. 24, 2015

(54) PORTABLE SPINAL ORTHOTIC BACKREST

(71) Applicant: Hoi Ming Michael Ho, Ontario (CA)

(72) Inventor: Hoi Ming Michael Ho, Ontario (CA)

(*) Notice: Subject to any disclaimer, the term of this patent is extended or adjusted under 35 U.S.C. 154(b) by 113 days.

(21) Appl. No.: 14/146,124

(22) Filed: Jan. 2, 2014

(65) Prior Publication Data

US 2015/0080994 A1 Mar. 19, 2015

(30) Foreign Application Priority Data

Sep. 18, 2013 (TW) .............................. 102133830 A

(51) Int. Cl.
| | | |
|---|---|---|
| *A47C 7/46* | (2006.01) | |
| *A61N 1/04* | (2006.01) | |
| *A61F 5/01* | (2006.01) | |
| *A61F 5/02* | (2006.01) | |
| *A47C 7/42* | (2006.01) | |

(52) U.S. Cl.
CPC ... *A47C 7/46* (2013.01); *A47C 7/42* (2013.01); *A61F 5/01* (2013.01); *A61F 5/02* (2013.01); *A61N 1/0456* (2013.01)

(58) Field of Classification Search
CPC ............ A47C 7/46; A47C 7/42; A47C 7/425; A47C 7/402; A61F 5/02; A61F 5/01; A61N 1/0456
See application file for complete search history.

(56) References Cited

U.S. PATENT DOCUMENTS 5,290,307 A * 3/1994 Choy ............................ 606/204
7,316,660 B1 * 1/2008 Modglin .......................... 602/5

* cited by examiner

*Primary Examiner* — Rex R Holmes
(74) *Attorney, Agent, or Firm* — Bacon & Thomas, PLLC

(57) ABSTRACT

The present invention is to provide a back support plate, which is integrally formed of plastic and includes an upper portion with an inner-side having a vertical curvature and a horizontal curvature that respectively conform to the curvature of human thoracic vertebrae and a horizontal curvature of the human back corresponding in position to the thoracic vertebrae, and a lower portion with an inner-side having a vertical curvature and a horizontal curvature that respectively conform to the curvature of human lumbar vertebrae and a horizontal curvature of the human back corresponding in position to the lumbar vertebrae. The two inner-sides are protrudingly provided with a plurality of protruding knobs which correspond in position to two lateral sides of the thoracic and lumbar vertebrae and have upwardly and downwardly decreasing widths, respectively, such that the joining section between the two portions extends to the two lateral sides of the human back.

6 Claims, 9 Drawing Sheets

PORTABLE SPINAL ORTHOTIC BACKREST

FIELD OF THE INVENTION

The present invention is to provide a backrest, more particularly to a portable spinal orthotic backrest integrally formed of plastic and including an upper portion and a lower portion, wherein the inner-sides of the upper and lower portions have vertical curvatures that respectively conform to the curvatures of human thoracic and lumbar vertebrae, are respectively provided with a plurality of protruding knobs which correspond in position to two lateral sides of the thoracic and lumbar vertebrae, and have upwardly and downwardly decreasing widths respectively, such that the joining section between the two portions extends to the two lateral sides of the human back. Since the portable spinal orthotic backrest is structurally simple and does not occupy much sitting space of a chair, it allow a user to have ample sitting space on the chair when being placed against the backrest of the chair and is able to properly and fully support the user's thoracic and lumbar vertebrae. Thus, the user's upper and lower back can be relaxed, and this upper- and lower-back muscle relaxing mechanism can help the user fine-tune the thoracic and lumbar vertebrae to their proper positions.

BACKGROUND OF THE INVENTION

According to surveys and research conducted by the present inventor, many white-collar workers, heavy computer users, and people who are required to sit long hours at work or performing their duties (e.g., drivers) tend to use backrests to support their upper and lower back and the surrounding muscle tissues, with a view to relieving the pressure on the spinal joints and spinal discs in the upper and lower back and the related muscle tissues, and to limiting the activity of the back and lumbar vertebrae so as to maintain the normal curvatures of the thoracic and lumbar vertebrae. It is intended that forces acting on the joints can be reduced, and muscles relaxed, by adjusting or correcting body postures. Backrests are also used to alleviate muscle fatigue and pain, promote blood circulation in back muscles, enhance the recovery of back muscle tissues, and relax muscles in the neck, the shoulders, and the upper and lower back so that the cervical, thoracic, and lumbar vertebrae can be gradually fine-tuned to their proper positions.

FIGS. 1 and 2 illustrate two of the most common backrests on the market, namely the short backrest 10 in FIG. 1 and the tall backrest 20 in FIG. 2. Both are made by covering a hard board with a bulky foam cushion and then enclosing the hard board and the foam cushion with a piece of mesh cloth made of nylon, Lycra, or other synthetic fibers. When the backrests 10 and 20 are newly made, their foam cushions conform to the configuration of the human back and therefore feel comfortable during use. When they are used for quite some time, however, almost all users will find the following drawbacks and deficiencies of the backrests 10 and 20 and use them no more:

(1) The curve of the hard board in either conventional backrest 10, 20—particularly the curve of the inner side (i.e., the user facing side) of the central longitudinal cross-section of the hard board—does not conform to the S-shaped curve jointly created by the kyphotic curve of the human thoracic spine and the lordotic curve of the human lumbar spine as shown in FIG. 3. Therefore, the hard boards themselves are totally incapable of properly and stably supporting the user's thoracic vertebrae T1~T12 and lumbar vertebrae L1~L5 and the surrounding muscle tissues. To compensate for this shortcoming of the conventional backrests 10 and 20, the hard boards are covered with the aforesaid foam cushions, whose configurations and elasticity can make the user feel that their upper and lower back is well supported. Nevertheless, this "feel" of support is only an imaginary support simulated by the foam cushions but not a substantial, proper, stable support. After long term use, the conventional backrests 10 and 20 tend to lose all their expected supporting abilities due to deformation of the foam cushions, or even cause the thoracic vertebrae T1~T12, the lumber vertebrae L1~L5, and the surrounding muscle tissues to shift to improper positions, which is contrary to the essential purpose of using the backrests 10 and 20: to fine-tune or correct the positions of the cervical vertebrae C1~C7, the thoracic vertebrae T1~T12, and the lumbar vertebrae L1~L5.

(2) The elasticity of the foam cushions, when new, often render the inner sides (i.e., the user facing sides) of the conventional backrests 10 and 20 too soft. Once the foam cushions show elastic fatigue after long term use, however, the inner sides of the backrests will become exceptionally stiff because of the material properties of the hard boards. In either case, the conventional backrests 10 and 20 fail to provide proper and stable support for the user's thoracic vertebrae T1~T12 and lumber vertebrae L1~L5 and the surrounding muscle tissues. Rather, the conventional backrests 10 and 20 are very likely to fatigue the foregoing vertebrae and muscle tissues by supporting them at the wrong positions. Should that happen, the user may adjust their sitting posture incorrectly, and an incorrect sitting posture may eventually shift the thoracic vertebrae T1~T12, the lumber vertebrae L1~L5, and the surrounding muscle tissues to improper positions.

(3) The conventional backrests 10 and 20 are bulky. When placed against the backrest of a chair, they tend to occupy so much sitting space that the user's buttocks cannot be correctly positioned. As a result, referring back to FIG. 3, the user's sacral vertebrae S will not form the normal S-shaped curve with the lumbar vertebrae L1~L5 and thoracic vertebrae T1~T12 above, and the surrounding muscle tissues will be tense and cannot be easily relaxed. In particular, when disposed against the backrest of the driver's seat in an automobile, the conventional backrests 10 and 20 often take up too much sitting space and thus deprive the user's buttocks of sufficient support, making it difficult for the user's feet to operate the throttle pedal or the brake pedal properly, which is dangerous.

(4) The conventional backrests 10 and 20 are seat cushions at best. While they provide a comfortable sitting environment at the beginning, they become useless as soon as the comfortable feel is gone. Discarding the backrests, however, is a waste of resources and environmentally unfriendly.

(5) The conventional backrests 10 and 20 are incapable of applying acupressure to the user's back. Nor can they be installed with electrodes which work with electrotherapy devices to electrically stimulate the acupoints on the user's back.

(6) Referring to FIGS. 1, 2, and 3, the conventional backrests 10 and 20 are not designed to support the user's cervical vertebrae C1~C7, and yet a twisted cervical spine may gradually shift the thoracic vertebrae T1~T12, the lumbar vertebrae L1~L5, and the surrounding muscle tissues to improper positions.

Hence, the issue to be addressed by the present invention is to design a novel backrest which overcomes the aforesaid problems, and compensates for the functional deficiencies, of the conventional backrests 10 and 20. It is desirable that the backrest is structurally simple, allows ample sitting space when placed against the backrest of a chair, and can properly and fully support the user's cervical vertebrae C1~C7, thoracic vertebrae T1~T12, and lumber vertebrae L1~L5, so as for the user to relax their neck, shoulders, upper and lower back, and the related muscle groups and thereby fine-tune the cervical vertebrae C1~C7, thoracic vertebrae T1~T12, and lumber vertebrae L1~L5 to their proper positions.

BRIEF SUMMARY OF THE INVENTION

In view of the aforesaid drawbacks and deficiencies of the conventional backrests, the inventor of the present invention conducted extensive research and experiment and finally succeeded in developing a portable spinal orthotic backrest as disclosed herein. Featuring a simple, compact, and multifunctional structural design, the disclosed backrest not only allows the user to have ample sitting space on a chair to which the backrest is applied, but also can provide proper and sufficient support for the user's cervical, thoracic, and lumber vertebrae.

It is an object of the present invention to provide a portable spinal orthotic backrest. The backrest includes a back support plate which is integrally formed of plastic and which includes, from top to bottom in a vertical direction, an upper portion and a lower portion. The upper portion has a vertical, central longitudinal cross-section whose inner-side curvature conforms to the curvature of human thoracic vertebrae, or more specifically the kyphotic curvature of the thoracic spine. The inner side of the upper portion is protrudingly provided with a plurality of protruding knobs which correspond in position to the two lateral sides of the thoracic vertebrae. The upper portion has a horizontal transverse cross-section whose inner-side curvature conforms to a horizontal curvature of the human back that corresponds in position to the thoracic vertebrae. The inner side of the upper portion is concave and has an upwardly decreasing width. The lower portion has a vertical, central longitudinal cross-section whose inner-side curvature conforms to the curvature of human lumbar vertebrae, or more specifically the lordotic curvature of the lumbar spine. The inner side of the lower portion is protrudingly provided with a plurality of protruding knobs which correspond in position to the two lateral sides of the lumbar vertebrae. The lower portion has a horizontal transverse cross-section whose inner-side curvature conforms to a horizontal curvature of the human back that corresponds in position to the lumbar vertebrae. The inner side of the lower portion is concave and has a downwardly decreasing width such that the joining section between the upper portion and the lower portion extends to the two lateral sides of the human back that are adjacent to the joining section between the bottom end of the thoracic vertebrae and the upper end of the lumbar vertebrae. The backrest is structurally simple and does not occupy much space. Therefore, when placed against the backrest of a chair where the user is seated, the backrest of the present invention allows ample sitting space on the chair and can properly and fully support the user's thoracic and lumbar vertebrae. Meanwhile, the protruding knobs can apply acupressure to the muscle tissues on the two lateral sides of the thoracic and lumbar vertebrae. Thus, the user's upper and lower back can be relaxed, and this upper- and lower-back muscle relaxing mechanism can help the user fine-tune the thoracic and lumbar vertebrae to their proper positions.

Another object of the present invention is to provide the foregoing portable spinal orthotic backrest, wherein the backrest further includes at least two suspension braces vertically installed on the backside of the back support plate. The two ends of each suspension brace are fixed to the upper portion and the lower portions respectively such that the suspension braces extend across the joining section between the upper portion and the lower portion and can prevent the portion of the back support plate that is adjacent to the joining section between the thoracic vertebrae and the lumbar vertebrae from deformation. The suspension braces also give the upper portion and the lower portion a predetermined amount of resilience with respect to the joining section between the upper and lower portions, turning the back support plate into a leaf-spring structure longitudinally. This ensures that the user's thoracic and lumbar vertebrae can move normally with respect to the joining section therebetween while maintaining the normal S-shaped curve.

Still another object of the present invention is to provide the foregoing portable spinal orthotic backrest, wherein the backrest further includes a position adjusting member and a cervical vertebrae support plate. The position adjusting member is installed on the backside of the back support plate and is adjacent to the top edge of the upper portion. The position adjusting member has a vertically extending connection hole and is provided with a height adjusting mechanism. The cervical vertebrae support plate, which is integrally formed of plastic, has a central longitudinal cross-section whose innerside curvature conforms to the curvature of human cervical vertebrae. The inner side of the cervical vertebrae support plate is protrudingly provided with a plurality of protruding knobs which correspond in position to the two lateral sides of the cervical vertebrae. In addition, the cervical vertebrae support plate is fixedly provided with a positioning bar. The positioning bar has one end fixed to the backside or bottom edge of the cervical vertebrae support plate and the opposite end extending beyond the bottom edge of the cervical vertebrae support plate in order to be inserted into the connection hole. Once the cervical vertebrae support plate is connected to the connection hole, the height of the cervical vertebrae support plate relative to the back support plate can be adjusted through the height adjusting mechanism. As the cervical vertebrae support plate can be installed on the back support plate as needed and be adjusted to suit the user's height, the cervical vertebrae support plate and the back support plate can jointly provide proper and full support for the user's cervical, thoracic, and lumbar vertebrae, allowing the user to relax the muscles in the neck, the shoulders, and the upper and lower back. This neck, shoulder, upper-back, and lower-back muscle relaxing mechanism will assist in fine-tuning the cervical, thoracic, and lumbar vertebrae to their proper positions.

Yet another object of the present invention is to provide the foregoing portable spinal orthotic backrest, wherein the back support plate is embedded with at least one conductive metal element. The conductive metal element is enclosed in the plastic of the back support plate and has one end electrically connectable to a transcutaneous electrical nerve stimulation (TENS) device. Besides, the top end of each protruding knob is provided with an electrode electrically connected to the other end of the conductive metal element (hereinafter referred to as the second end of the conductive metal element). The electrodes can receive electrotherapy signals from the TENS device through the conductive metal element in order to perform electrotherapy on the corresponding muscles in the user's upper and lower back when the user is sitting on a chair against whose backrest the portable spinal orthotic backrest of the present invention is placed.

A further object of the present invention is to provide the foregoing portable spinal orthotic backrest, wherein the top end of each protruding knob is concavely provided with an installation recess, and the second end of the conductive metal element is exposed through the bottom portion of each installation recess. Moreover, the bottom end of each electrode is protrudingly provided with a magnet. When the magnets are respectively disposed in the installation recesses and magnetically attached to the second end of the conductive metal element, the top ends of the electrodes jut out of the installation recesses in order to perform electrotherapy on the corresponding muscles in the user's upper and lower back.

BRIEF DESCRIPTION OF THE SEVERAL VIEWS OF THE DRAWINGS

The objects, as well as the technical features and their effects, of the present invention will be best understood by referring to the following detailed description of some illustrative embodiments in conjunction with the accompanying drawings, in which.

DETAILED DESCRIPTION OF THE INVENTION

The inventor has long been engaged in research and development of medical assistive devices. In the process, the inventor has found that the conventional portable backrests are bulky and tend to occupy too much sitting space during use. Consequently, one who places such a portable backrest against the backrest of a chair and sits in the reduced sitting space of the chair cannot have their thoracic and lumbar vertebrae properly and fully supported by the portable backrest. In light of this, the inventor came up with the idea of designing a thin, simple, and multifunctional backrest which, when used on a chair, allows amble sitting space and can properly and fully support the user's cervical, thoracic, and lumbar vertebrae, allowing the user to relax the muscles in the neck, the shoulders, and the upper and lower back and, with the assistance of such a muscle relaxing mechanism, fine-tune the foregoing vertebrae to their proper positions.

Figure 1:
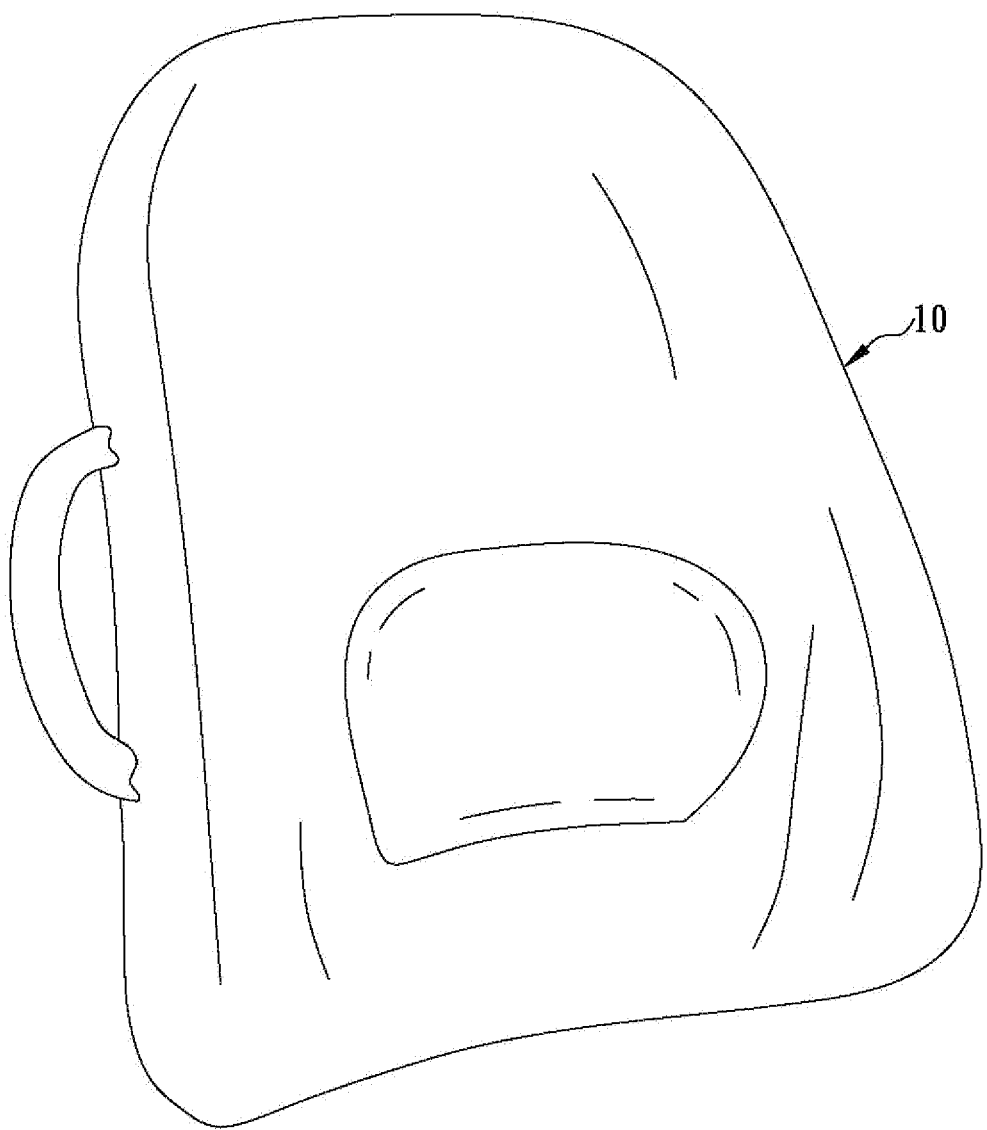
FIG. 1 is a perspective view of a conventional short backrest.
Figure 2:
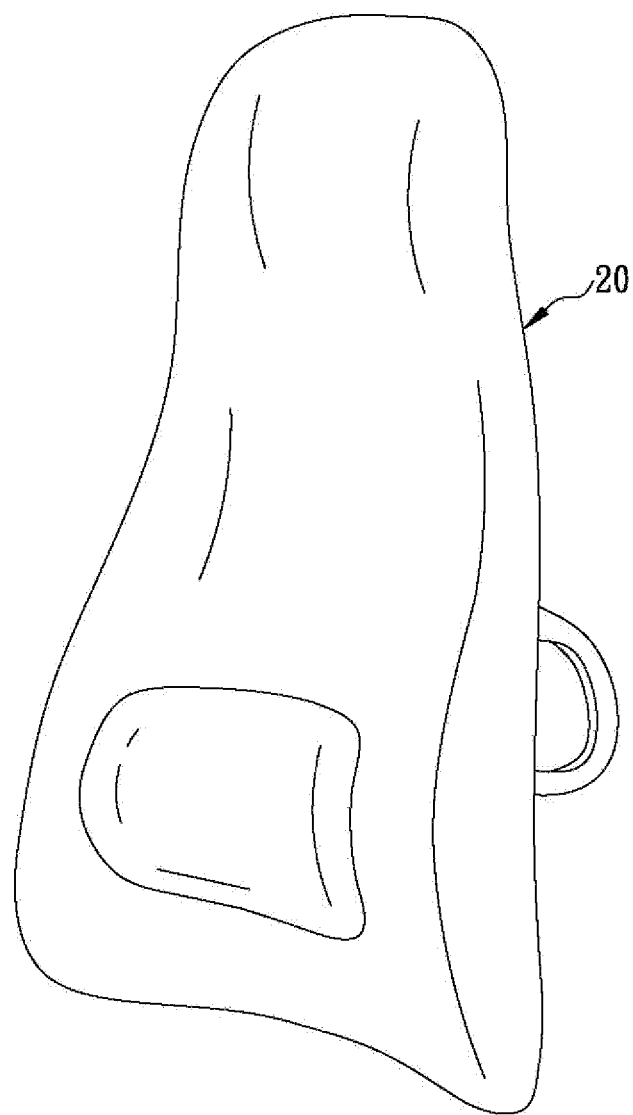
FIG. 2 is a perspective view of a conventional tall backrest.
Figure 3:
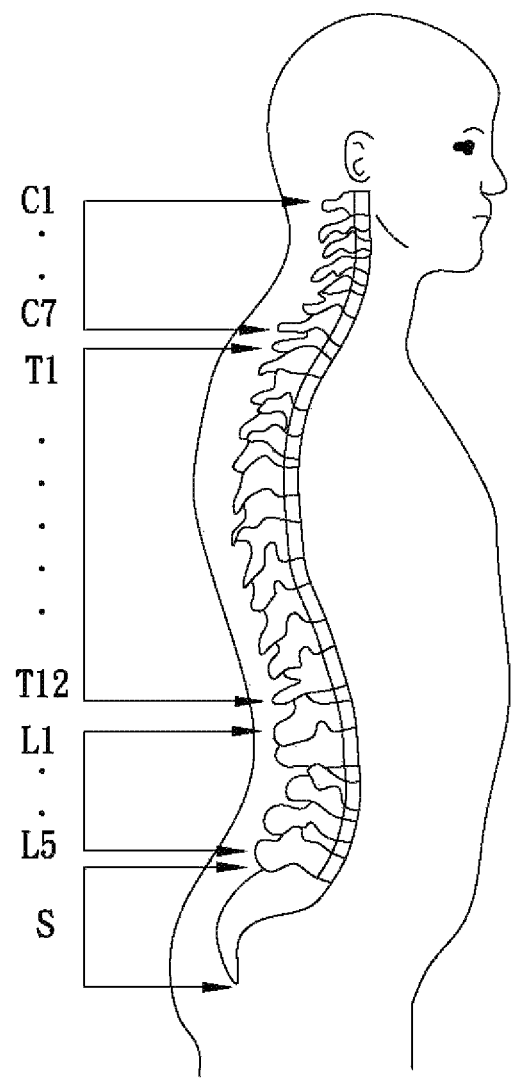
FIG. 3 is a schematic side view of the human spine structure.
Figure 4:
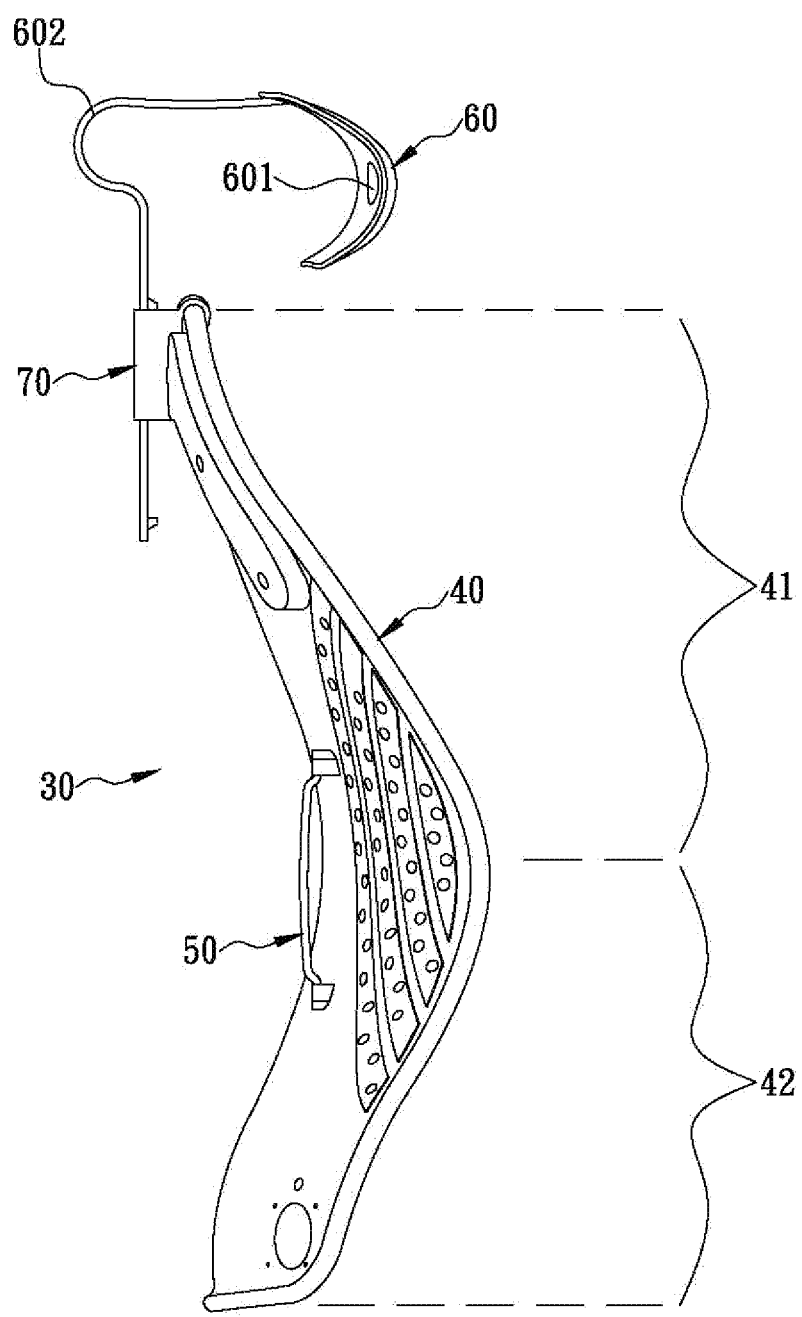
FIG. 4 is a side view of a preferred embodiment of the present invention.
Figure 5:
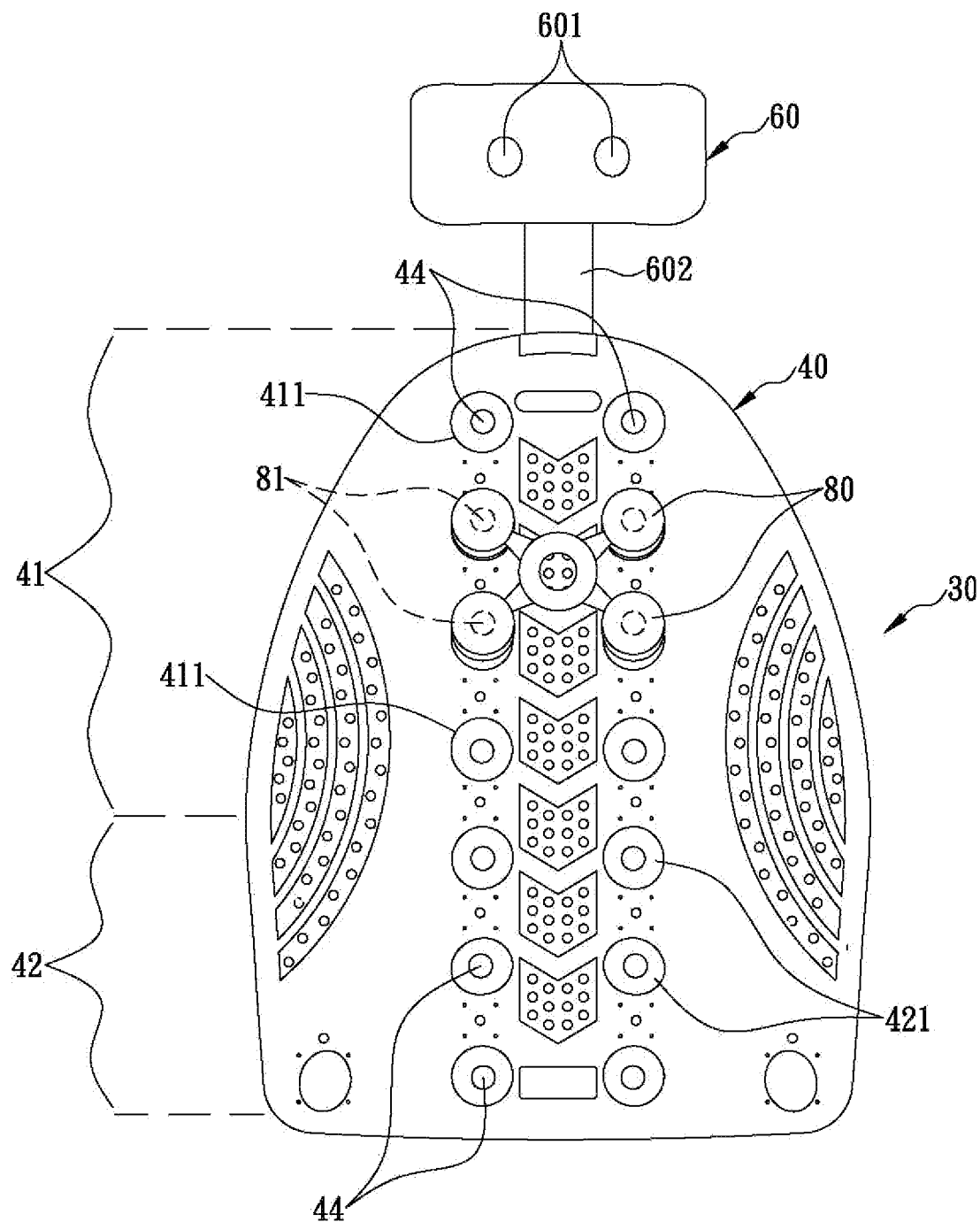
FIG. 5 is a front view of a preferred embodiment of the present invention.
Figure 6:
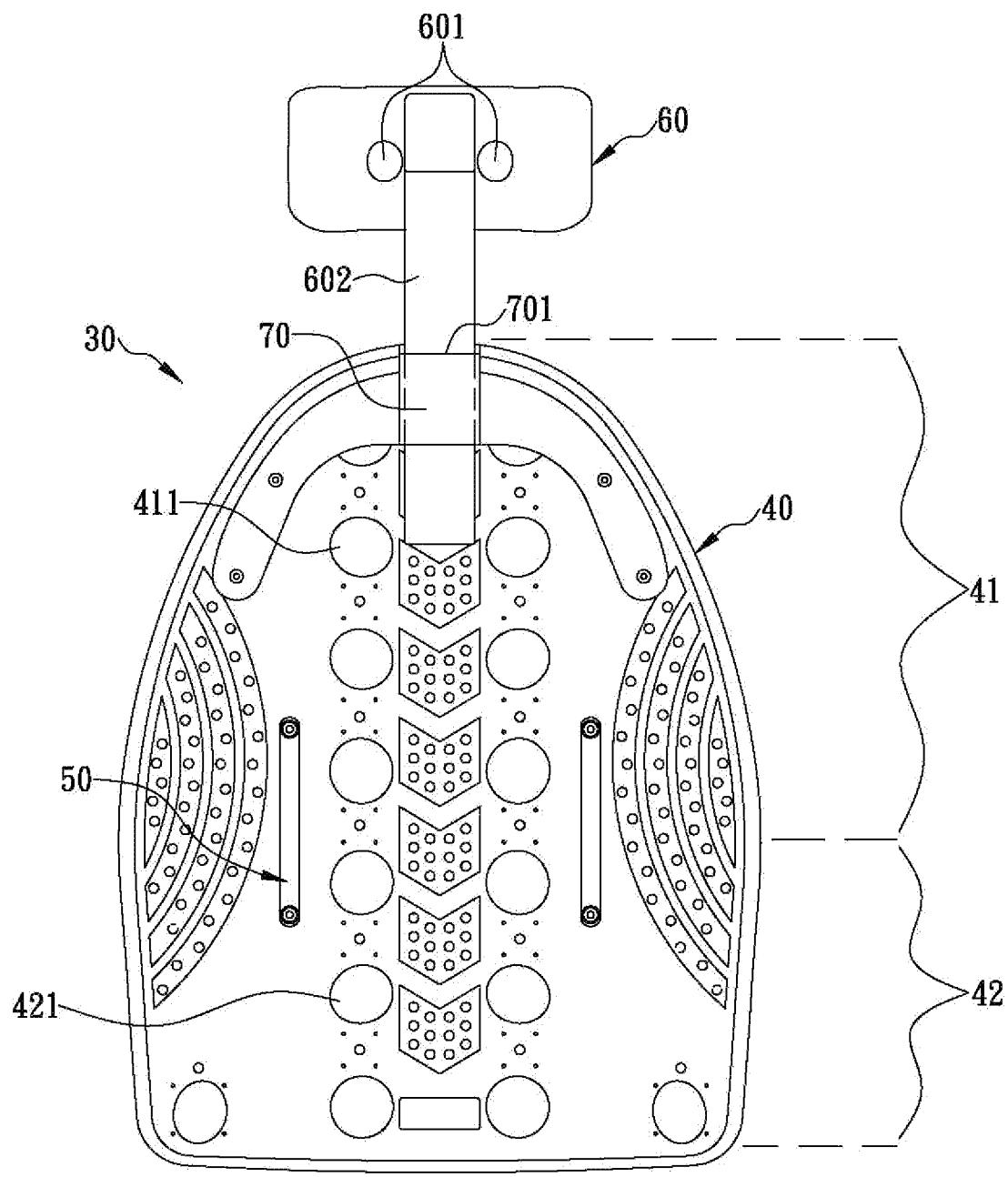
FIG. 6 is a rear view of a preferred embodiment of the present invention.
Figure 7:
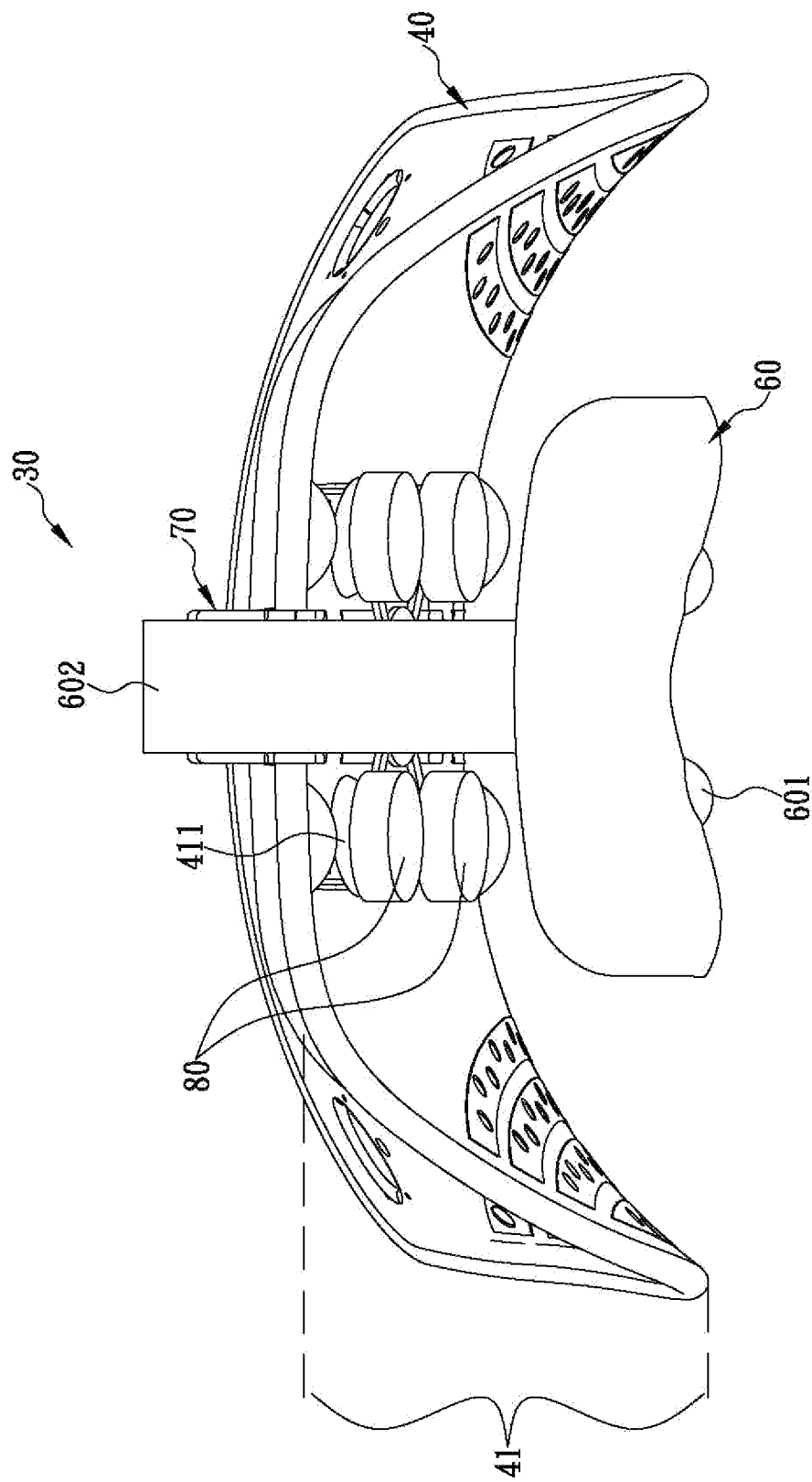
FIG. 7 is a top view of a preferred embodiment of the present invention.
Figure 8:
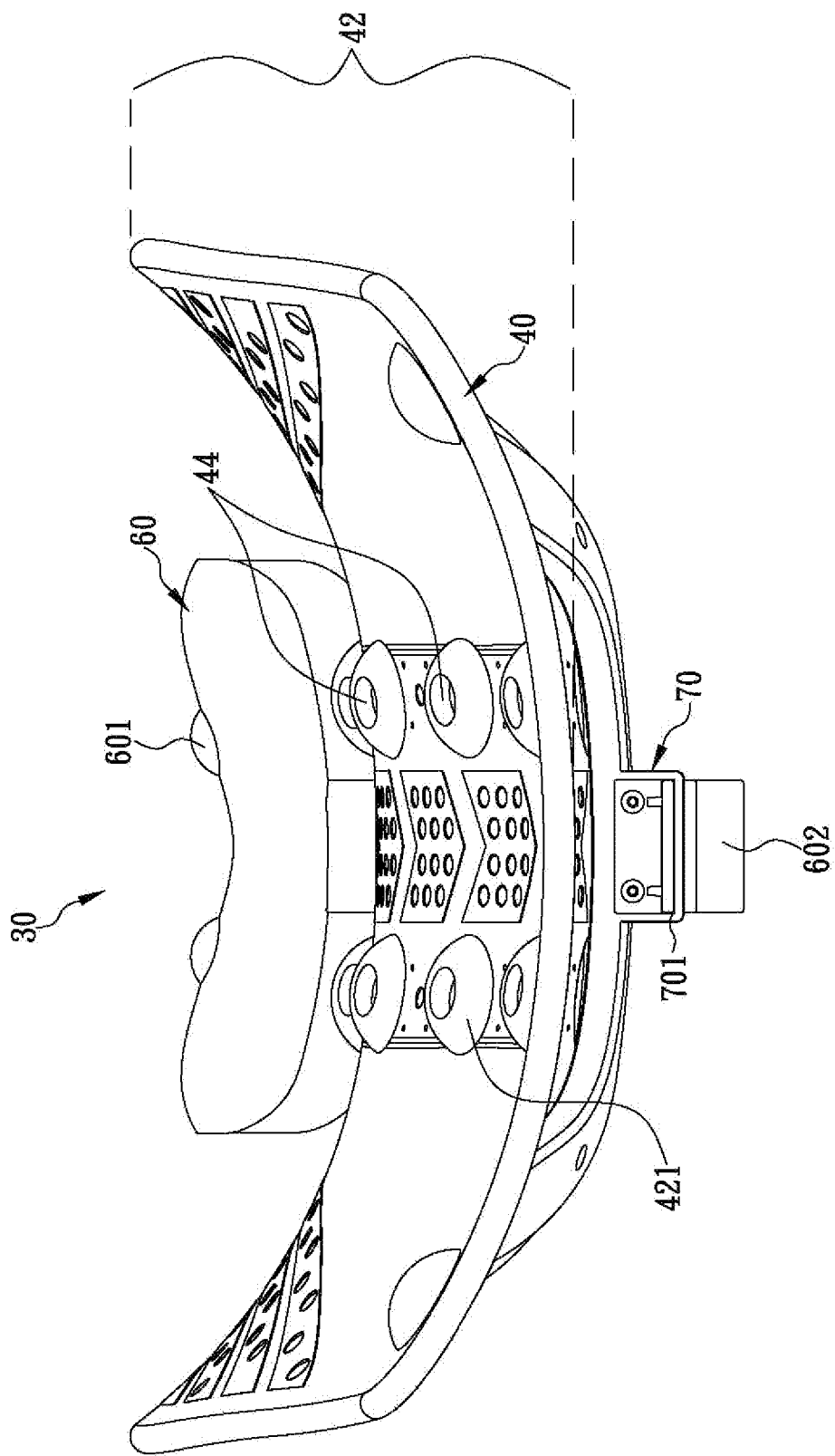
FIG. 8 is a bottom view of a preferred embodiment of the present invention.

The present invention discloses a portable spinal orthotic backrest. Please refer to FIGS. 4, 5, and 6 respectively for a side view, a front view, and a rear view of the backrest 30 in a preferred embodiment of the present invention, wherein the backrest 30 includes a back support plate 40. The back support plate 40 is integrally formed of a plastic material and includes two portions arranged from top to bottom in a vertical direction, namely the upper portion 41 and the lower portion 42. The upper portion 41 has a vertical, central longitudinal cross-section whose inner-side curvature conforms to the curvature of the human thoracic vertebrae, or more specifically the kyphotic curvature of the thoracic spine. The inner side of the upper portion 41 is protrudingly provided with a plurality of protruding knobs 411 which correspond in position to the two lateral sides of the thoracic vertebrae. Referring to FIG. 7 for a top view of the backrest 30, the upper portion 41 has a horizontal transverse cross-section whose inner-side curvature conforms to a horizontal curvature of the human back that corresponds in position to the thoracic vertebrae. The inner side of the upper portion 41 is concave and is narrower at the top than at the bottom. As shown in FIGS. 4, 5, and 6, the lower portion 42 has a vertical, central longitudinal cross-section whose inner-side curvature conforms to the curvature of the human lumbar vertebrae, or more specifically the lordotic curvature of the lumbar spine. The inner side of the lower portion 42 is protrudingly provided with a plurality of protruding knobs 421 which correspond in position to the two lateral sides of the lumbar vertebrae. Referring to FIG. 8 for a bottom view of the backrest 30, the lower portion 42 has a horizontal transverse cross-section whose inner-side curvature conforms to a horizontal curvature of the human back that corresponds in position to the lumbar vertebrae. The inner side of the lower portion 42 is concave and is wider at the top than at the bottom. Thus, the joining section between the upper portion 41 and the lower portion 42 extends to the two lateral sides of the human back that are adjacent to the joining section between the bottom end of the thoracic vertebrae and the top and of the lumbar vertebrae. As the backrest 30 is structurally simple and does not occupy much space, it can be placed against the backrest of a chair but still allows the user to have ample sitting space on the chair. Not only that, the back support plate 40 can provide proper and full support for the user's thoracic and lumbar vertebrae. The top ends of the protruding knobs 411 and 421, on the other hand, can massage, or apply acupressure to, the muscle tissues on the two lateral sides of the thoracic and lumbar vertebrae respectively. The foregoing technical features allow the user to relax the muscles in the upper and lower back and, with the assistance of this upper- and lower-back muscle relaxing mechanism, to fine-tune the thoracic and lumbar vertebrae to their proper positions. In this embodiment, in which the back support plate 40 is integrally formed of a plastic material, the upper portion 41 and the lower portion 42 function as a leaf spring, thanks to the configurations of those portions and the elasticity and supporting property of the plastic material. The upper portion 41 and the lower portion 42 not only can provide uniform and full support for the part of the user's back that corresponds in position to the thoracic and lumbar vertebrae, but also can generate a restoring force within the backrest 30 when deformed by improper force application. The restoring force will drive the upper portion 41 and the lower portion 42 to resume their original configurations featuring the perfect S-shaped curve of the thoracic and lumbar vertebrae.

Referring to FIGS. 4, 5, and 6, the backrest 30 further includes at least two suspension braces 50. Each suspension brace 50 is made of a metal or a rigid plasticized material and has such structural strength that it will not easily deform. The suspension braces 50 are installed on the backside of the back support plate 40 along the vertical direction, and each suspension brace 50 has its two ends respectively fixed to the upper portion 41 and the lower portion 42. Thus, the suspension braces 50 extend across the joining section between the upper portion 41 and the lower portion 42 and can prevent deformation of the part of the back support plate 40 that is adjacent to the joining section between the thoracic vertebrae and the lumbar vertebrae. Moreover, due to the suspension braces 50, the upper portion 41 and the lower portion 42 have a predetermined amount of resilience with respect to the joining section therebetween, and the back support plate 40 can therefore be viewed as a leaf-spring structure both longitudinally and transversely. This ensures that the user's thoracic vertebrae and lumbar vertebrae can move with respect to the joining section therebetween in a normal manner while maintaining the normal S-shaped configuration.

Referring to FIGS. 4, 5, and 6, the backrest 30 further includes a cervical vertebrae support plate 60 and a position adjusting member 70. The position adjusting member 70 is installed on the backside of the back support plate 40 and is adjacent to the top edge of the upper portion 41. The position adjusting member 70 is provided with a connection hole 701 which extends in the vertical direction. The position adjusting member 70 is also provided therein with a height adjusting mechanism (not shown). The cervical vertebrae support plate 60 is integrally formed of a plastic material and has a central longitudinal cross-section whose inner-side curvature conforms to the curvature of the human cervical vertebrae. Referring again to FIGS. 7 and 8, the cervical vertebrae support plate 60 has a horizontal transverse cross-section whose inner-side curvature conforms to a horizontal curvature of the human neck that corresponds in position to the cervical vertebrae. The inner side of the cervical vertebrae support plate 60 is concave and is protrudingly provided with a plurality of protruding knobs 601 which correspond in position to the two lateral sides of the cervical vertebrae. In addition, the cervical vertebrae support plate 60 is fixedly provided with a positioning bar 602. One end of the positioning bar 602 is fixed at the backside or bottom edge of the cervical vertebrae support plate 60. The other end of the positioning bar 602 extends beyond the bottom edge of the cervical vertebrae support plate 60 and can be inserted into the connection hole 701 so that the height of the cervical vertebrae support plate 60 relative to the back support plate 40 can be adjusted via the height adjusting mechanism (not shown). The cervical vertebrae support plate 60 can be installed on the back support plate 40 as desired and be adjusted according to the user's height in order for the cervical vertebrae support plate 60 and the back support plate 40 to properly and fully support the user's cervical, thoracic, and lumbar vertebrae, allowing the user to relax the muscles in the neck, the shoulders, and the upper and lower back. With the assistance of this mechanism for relaxing the muscles in the neck, the shoulders, and the upper and lower back, the user's cervical, thoracic, and lumbar vertebrae can be gradually fined-tuned to their proper positions.

Figure 9:
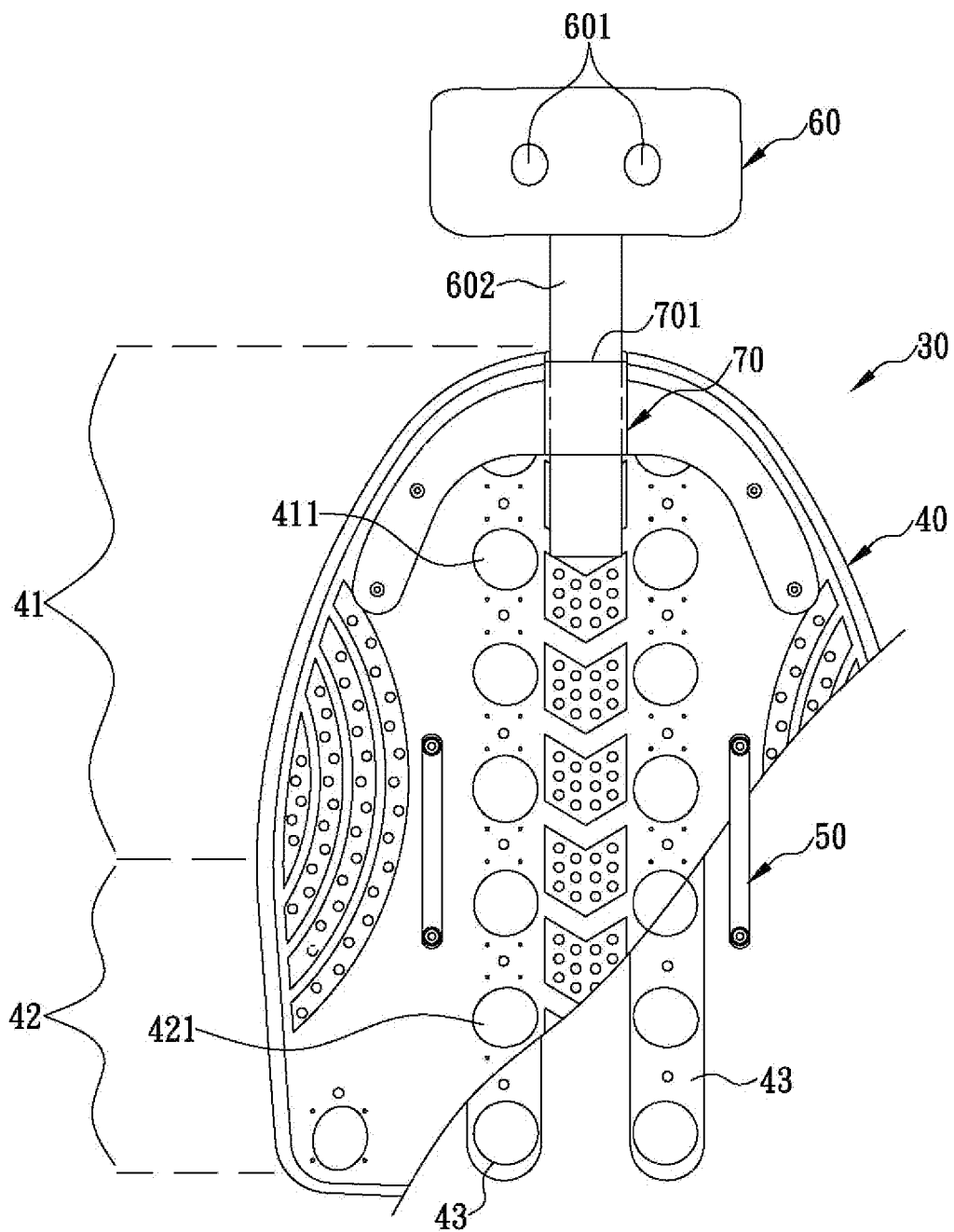
FIG. 9 is a partially sectional rear view of a preferred embodiment of the present invention.

Referring to FIG. 9 for a rear view of the backrest 30, the back support plate 40 further has at least one conductive metal element 43 embedded therein. The conductive metal elements 43 are enclosed in the plastic material of the back support plate 40 and are electrically connected at one end to a transcutaneous electrical nerve stimulation (TENS) device (not shown). Referring back to FIGS. 5 and 7, the top end of each protruding knob 411, 421 is provided with an electrode 80, and each electrode 80 is electrically connected to the other end (hereinafter referred to as the second end) of the corresponding conductive metal element 43. The electrodes 80 can receive electrotherapy signals from the TENS device through the corresponding conductive metal elements 43 so as to perform electrotherapy on the corresponding muscles in the user's upper and lower back when the user is seated on a chair against whose backrest is placed the backrest 30.

As shown in FIG. 5, the top end of each protruding knob 411, 421 is concavely provided with an installation recess 44, and the second end of each conductive metal element 43 is exposed through the bottom portion of each corresponding installation recess 44. Moreover, the bottom end of each electrode 80 is protrudingly provided with a magnet 81. When the magnets 81 are respectively placed in the installation recesses 44 and magnetically attached to the second ends of the conductive metal elements 43, the top ends of the electrodes 80 protrude from the respective installation recesses 44 in order to perform electrotherapy on the muscles in the user's neck, shoulders, and upper and lower back.

According to the above, the backrest 30 of the present invention not only is structurally simple and space-efficient, but also has the following functions and advantages:

(1) The dimensions of the backrest 30 can be tailored for different classes of statures and body shapes, wherein the backrest configuration for each class corresponds to the average stature and body shape of that class. More specifically, the back support plate 40 for each class is configured to conform to the average shape of human backs in that class and have a vertical, central longitudinal cross-section whose inner-side curvature conforms, from top to bottom, to the curvatures of the human thoracic and lumbar vertebrae, i.e., the kyphotic curvature of the thoracic spine and the lordotic curvature of the lumbar spine, in order for the inner side of the aforesaid cross-section to have a perfect S-shaped curve. The back support plate 40 can therefore provide proper and stable support for the user's thoracic and lumbar vertebrae and the surrounding muscle tissues. Not only will the user feel their back fully supported in the area corresponding to the thoracic and lumbar vertebrae, but also the feel of support stems from a substantial, proper, and stable support provided by the back support plate 40. Hence, after long term use, the backrest 30 of the present invention will not deform but will keep providing sufficient support for the user's thoracic and lumbar vertebrae, allowing the user to relax the surrounding muscle tissues and thereby fine-tune the thoracic and lumbar vertebrae to their proper positions.

(2) The back support plate 40 of the present invention is integrally formed of plastic and therefore, in addition to being resilient and resistant to permanent deformation, is easy to carry and space-efficient due to its thinness and light weight. Even if the back support plate 40 has been used for a long time, it is still capable of and effective in providing proper and stable support for the user's thoracic and lumbar vertebrae and the surrounding muscle tissues, thereby keeping the user from muscle fatigue and consequently from wrongly adjusting their sitting posture. As stated above, an incorrect sitting posture may in the long run shift the thoracic vertebrae, the lumbar vertebrae, and the surrounding muscle tissues to improper positions.

(3) The back support plate 40 of the present invention has a thin and simple structure. Once the user places the back support plate 40 against the backrest of a chair and sits on that chair, leaning back, the back support plate 40 is pressed compliantly against the chair backrest and occupies little sitting space of the chair, allowing the user's buttocks to stay correctly positioned. Thus, it can be ensured that the user's sacral vertebrae and the lumbar and thoracic vertebrae above will always assume a perfect S shape and that the surrounding muscle tissues will not be tense but easily relaxed. In particular, when placed against the backrest of the driver's seat of a car, the back support plate 40 takes up little sitting space of the car seat such that the user's buttocks are sufficiently supported to enable proper operation of the throttle pedal or the brake pedal by the user's feet, which in turn ensures driving safety.

(4) The cervical vertebrae support plate 60 of the present invention is also integrally formed of plastic and hence lightweight and structurally simple. When the back support plate 40 installed with the cervical vertebrae support plate 60 is disposed against the backrest of a chair, the cervical vertebrae support plate 60 can be adjusted as appropriate to suit the user's height, in order for the cervical vertebrae support plate 60 and the back support plate 40 to properly and fully support the user's cervical, thoracic, and lumbar vertebrae, thereby allowing the user to relax the muscles in the neck, the shoulders, and the upper and lower back and, with the assistance of such a mechanism for relaxing the foregoing muscles, fine-tune the cervical, thoracic, and lumbar vertebrae to their proper positions.

(5) In the present invention, the back support plate 40 and the cervical vertebrae support plate 60 are respectively and protrudingly provided with the protruding knobs 421, 411, which correspond in position to the muscle tissues on the lateral sides of the lumbar and thoracic vertebrae, and the protruding knobs 601, which correspond in position to the muscle tissues on the lateral sides of the cervical vertebrae. The protruding knobs 421, 411, and 601 serve to apply acupressure to the muscle tissues on the lateral sides of the lumbar, thoracic, and cervical vertebrae while the back support plate 40 and the cervical vertebrae support plate 60 provide proper and full support for the same vertebrae. This allows the user to relax, and relieve from fatigue, the muscles in the neck, the shoulders, and the upper and lower back and, with the assistance of such a mechanism for relaxing the foregoing muscles, fine-tune the cervical, thoracic, and lumbar vertebrae to their proper positions.

(6) The electrodes 80 provided on the protruding knobs 421 and 411 of the back support plate 40 can be used to perform electrotherapy on the muscle tissues and acupoints on the lateral sides of the user's lumbar and thoracic vertebrae while the back support plate 40 provides proper and full support for the same vertebrae. The stimulation of the electrotherapy is intended to further relax the muscles in the user's upper and lower back.

(7) The electrodes 80 of the present invention are magnetically attached to the second ends of the conductive metal elements 43 via the magnets 81, with the top ends of the electrodes 80 jutting out of the installation recesses 44 to perform electrotherapy on the muscles in the user's upper and lower back. The user can freely select the locations at which to install the electrodes 80 so that electrotherapy is performed on the user's upper and lower back at positions where electrical stimulation is needed.

While the invention herein disclosed has been described by means of specific embodiments, numerous modifications and variations could be made thereto by those skilled in the art without departing from the scope of the invention set forth in the claims.

What is claimed is:

1. A portable spinal orthotic backrest, comprising a back support plate, the back support plate being integrally formed of a plastic material and comprising, from top to bottom in a vertical direction:
    an upper portion having a vertical, central longitudinal cross-section with an inner-side curvature conforming to a kyphotic curvature of a person's thoracic vertebrae, the upper portion having an inner side protrudingly provided with a plurality of protruding knobs corresponding in position to two lateral sides of the thoracic vertebrae, the upper portion having a horizontal transverse cross-section with an inner-side curvature conforming to a horizontal curvature of the person's back that corresponds in position to the thoracic vertebrae, the inner side of the upper portion being concave and having an upwardly decreasing width;
    a lower portion having a vertical, central longitudinal cross-section with an inner-side curvature conforming to a lordotic curvature of the person's lumbar vertebrae, the lower portion having an inner side protrudingly provided with a plurality of protruding knobs corresponding in position to two lateral sides of the lumbar vertebrae, the lower portion having a horizontal transverse cross-section with an inner-side curvature conforming to a horizontal curvature of the person's back that corresponds in position to the lumbar vertebrae, the inner side of the lower portion being concave and having a downwardly decreasing width such that a joining section between the upper portion and the lower portion extends to two lateral sides of the person's back that are adjacent to a joining section between a bottom end of the thoracic vertebrae and an upper end of the lumbar vertebrae; and
    at least a conductive metal element being embedded and enclosed in the plastic material of the back support plate and having an end electrically connected to a transcutaneous electrical nerve stimulation (TENS) device, wherein each said protruding knob has a top end provided with an electrode, and the electrodes are electrically connected to a second end of the conductive metal element in order to receive electrotherapy signals from the TENS device through the conductive metal element.

2. The portable spinal orthotic backrest of claim 1, wherein the top end of each said protruding knob is concavely provided with an installation recess, the second end of the conductive metal element is exposed through a bottom portion of each said installation recess, and each said electrode has a bottom end provided with a magnet such that, once the magnets are respectively placed in the installation recesses and magnetically attached to the second end of the conductive metal element, top ends of the electrodes protrude from the installation recesses.

3. A portable spinal orthotic backrest, comprising a back support plate, the back support plate being integrally formed of a plastic material and comprising, from top to bottom in a vertical direction:
    an upper portion having a vertical, central longitudinal cross-section with an inner-side curvature conforming to a kyphotic curvature of a person's thoracic vertebrae, the upper portion having an inner side protrudingly provided with a plurality of protruding knobs corresponding in position to two lateral sides of the thoracic vertebrae, the upper portion having a horizontal transverse cross-section with an inner-side curvature conforming to a horizontal curvature of the person's back that corresponds in position to the thoracic vertebrae, the inner side of the upper portion being concave and having an upwardly decreasing width;
    a lower portion having a vertical, central longitudinal cross-section with an inner-side curvature conforming to a lordotic curvature of the person's lumbar vertebrae, the lower portion having an inner side protrudingly provided with a plurality of protruding knobs corresponding in position to two lateral sides of the lumbar vertebrae, the lower portion having a horizontal transverse cross-section with an inner-side curvature conforming to a horizontal curvature of the person's back that corresponds in position to the lumbar vertebrae, the inner side of the lower portion being concave and having a downwardly decreasing width such that a joining section between the upper portion and the lower portion extends to two lateral sides of the person's back that are adjacent to a joining section between a bottom end of the thoracic vertebrae and an upper end of the lumbar vertebrae;
    at least two suspension braces made of a metal or a rigid plasticized material and installed on a backside of the back support plate along the vertical direction, wherein each said suspension brace has two ends respectively fixed to the upper portion and the lower portion such that each said suspension brace extends across the joining section between the upper portion and the lower portion; and at least a conductive metal element being embedded and enclosed in the plastic material of the back support plate and having an end electrically connected to a transcutaneous electrical nerve stimulation (TENS) device, wherein each said protruding knob has a top end provided with an electrode, and the electrodes are electrically connected to a second end of the conductive metal element in order to receive electrotherapy signals from the TENS device through the conductive metal element.

4. The portable spinal orthotic backrest of claim 3, wherein the top end of each said protruding knob is concavely provided with an installation recess, the second end of the conductive metal element is exposed through a bottom portion of each said installation recess, and each said electrode has a bottom end provided with a magnet such that, once the magnets are respectively placed in the installation recesses and magnetically attached to the second end of the conductive metal element, top ends of the electrodes protrude from the installation recesses.

5. A portable spinal orthotic backrest, comprising a back support plate, the back support plate being integrally formed of a plastic material and comprising, from top to bottom in a vertical direction:

an upper portion having a vertical, central longitudinal cross-section with an inner-side curvature conforming to a kyphotic curvature of a person's thoracic vertebrae, the upper portion having an inner side protrudingly provided with a plurality of protruding knobs corresponding in position to two lateral sides of the thoracic vertebrae, the upper portion having a horizontal transverse cross-section with an inner-side curvature conforming to a horizontal curvature of the person's back that corresponds in position to the thoracic vertebrae, the inner side of the upper portion being concave and having an upwardly decreasing width;

a lower portion having a vertical, central longitudinal cross-section with an inner-side curvature conforming to a lordotic curvature of the person's lumbar vertebrae, the lower portion having an inner side protrudingly provided with a plurality of protruding knobs corresponding in position to two lateral sides of the lumbar vertebrae, the lower portion having a horizontal transverse cross-section with an inner-side curvature conforming to a horizontal curvature of the person's back that corresponds in position to the lumbar vertebrae, the inner side of the lower portion being concave and having a downwardly decreasing width such that a joining section between the upper portion and the lower portion extends to two lateral sides of the person's back that are adjacent to a joining section between a bottom end of the thoracic vertebrae and an upper end of the lumbar vertebrae;

a position adjusting member installed on a backside of the back support plate and being adjacent to a top edge of the upper portion, the position adjusting member having a connection hole extending in the vertical direction, the position adjusting member being provided therein with a height adjusting mechanism;

a cervical vertebrae support plate integrally formed of a plastic material, the cervical vertebrae support plate having a vertical, central longitudinal cross-section with an inner-side curvature conforming to a curvature of the person's cervical vertebrae, the cervical vertebrae support plate having a horizontal transverse cross-section with an inner-side curvature conforming to a horizontal curvature of the person's neck that corresponds in position to the cervical vertebrae, the cervical vertebrae support plate having a concave inner side protrudingly provided with a plurality of protruding knobs corresponding in position to two lateral sides of the cervical vertebrae, the cervical vertebrae support plate being fixedly provided with a positioning bar, wherein the positioning bar has an end fixed to a backside or a bottom edge of the cervical vertebrae support plate and has an opposite end extending beyond the bottom edge of the cervical vertebrae support plate and insertable into the connection hole so that a height of the cervical vertebrae support plate relative to the back support plate can be adjusted via the height adjusting mechanism; and at least a conductive metal element being embedded and enclosed in the plastic material of the back support plate and having an end electrically connected to a transcutaneous electrical nerve stimulation (TENS) device, wherein each said protruding knob has a top end provided with an electrode, and the electrodes are electrically connected to a second end of the conductive metal element in order to receive electrotherapy signals from the TENS device through the conductive metal element.

6. The portable spinal orthotic backrest of claim 5, wherein the top end of each said protruding knob is concavely provided with an installation recess, the second end of the conductive metal element is exposed through a bottom portion of each said installation recess, and each said electrode has a bottom end provided with a magnet such that, once the magnets are respectively placed in the installation recesses and magnetically attached to the second end of the conductive metal element, top ends of the electrodes protrude from the installation recesses.

* * * * *